United States Patent [19]
Ransford

[11] Patent Number: 4,836,193
[45] Date of Patent: Jun. 6, 1989

[54] SKULL TO SPINE FIXATION DEVICE

[75] Inventor: Andrew O. Ransford, London, England

[73] Assignee: A. W. Showell (Surgicraft) Limited, Redditch, England

[21] Appl. No.: 116,457

[22] Filed: Nov. 3, 1987

[30] Foreign Application Priority Data

Nov. 5, 1986 [GB] United Kingdom ............... 8626409

[51] Int. Cl.⁴ .......................... A61F 5/04; A61F 5/08
[52] U.S. Cl. .................................. 128/69; 128/76 R; 128/92 YM; 128/92 YD; 623/17
[58] Field of Search ................ 623/17; 128/69, 92 R, 128/92 YM, 92 YD, 92 YE, 92 Y, 92 YS, 92 V, 92 YF, 75, 76 R, 87 B, 87 C

[56] References Cited

U.S. PATENT DOCUMENTS

| 1,301,276 | 4/1919 | Koetz | 128/76 R X |
| 4,573,454 | 3/1986 | Hoffman | 128/92 YM |
| 4,643,174 | 2/1987 | Horiuchi | 128/76 R |
| 4,686,970 | 8/1987 | Dove et al. | 128/92 YM |
| 4,738,251 | 4/1988 | Plaza | 128/69 |

FOREIGN PATENT DOCUMENTS

| 2293183 | 7/1976 | France | 128/92 YF |
| 548268 | 4/1977 | U.S.S.R. | 128/92 YM |
| 0706080 | 1/1980 | U.S.S.R. | 128/92 YM |
| 2151928 | 7/1985 | United Kingdom . | |

Primary Examiner—Richard J. Apley
Assistant Examiner—David J. Bender
Attorney, Agent, or Firm—R. A. Giangiorgi

[57] ABSTRACT

A device (10B) for fixation of a skull (20) to adjacent bones (21) of the spine has one generally circular bight (13B) in a curved plane starting generally perpendicular to the plane of two straight spaced coplanar portions (11B) and curving away therefrom, and another bight (12B) of generally V-shape with its apex (14B) extending towards the substantially circular bight (13B) so that the apex (14B) of the V-shaped bight can be accommodated between the adjacent spinous processes (16D, 16E) closest to the skull (20) against which the generally circular bight (13B) lies.

1 Claim, 2 Drawing Sheets

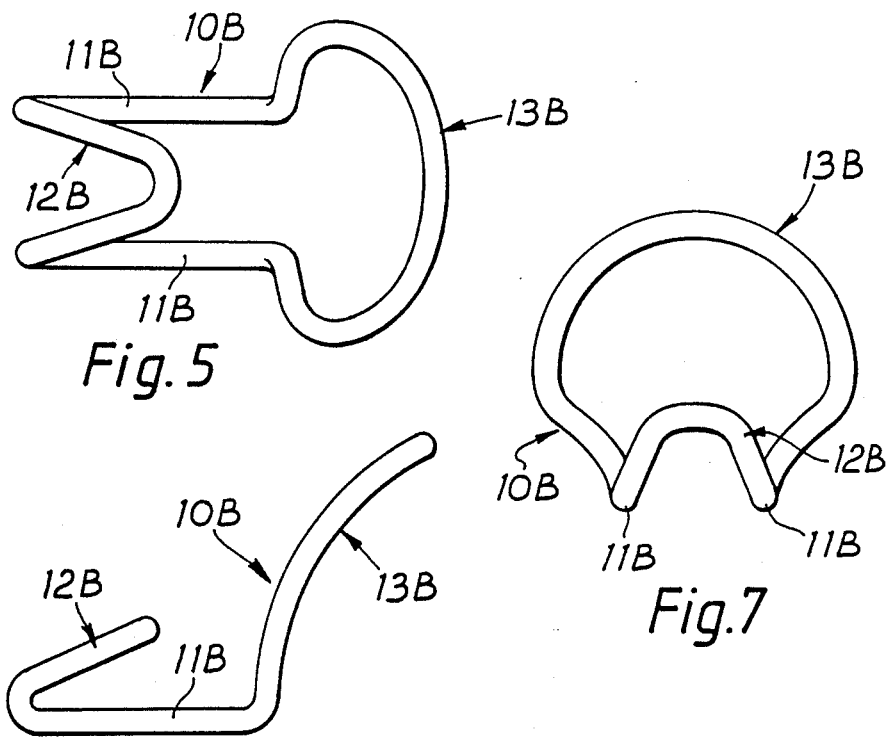
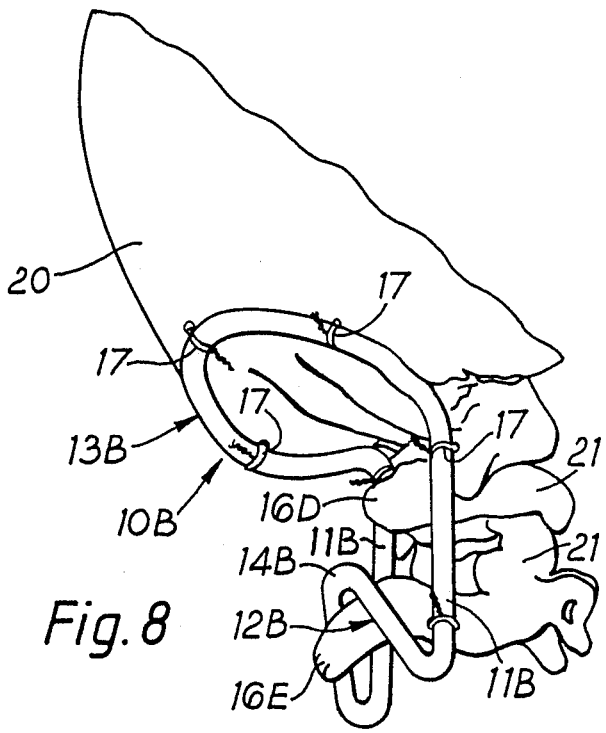

SKULL TO SPINE FIXATION DEVICE

BACKGROUND OF THE INVENTION

This invention relates to devices for spinal etc. fixation, of which one known type (GB-PS 2 151 928A) consists of stainless steel or titanium round rod of 3/16" or 4.7625 mm diameter formed into a rigid rectangle with its shorter sides bent (e.g. into or including a curve) in the same direction from the plane of the longer sides which are adapted to fit substantially parallel to the length of two or more bones of the spine with the shorter sides accommodated between respective pairs of adjacent spinous processes, the rectangle being fixed in place to immobilise the bones with respect to each other by means of wires or other strands around or looped through the rectangle and passing through holes in the bones.

The bending (and/or curving) of the shorter sides enables the longer sides of the "roofed" rectangle to fit more closely upon the transverse processes of the bones of the spine than the previously "flat" rectangle and therefore it appears less bulky. This reduces dead spaces between the device and the spine, thus effectively reducing the risk of haematoma and infection, whilst being biomechanically more efficient. Correct fixing of the "roofed" rectangle is more consistently obtained because wires or other strands looped through the rectangle round the shorter sides are automatically guided down the "slopes" of the shorter sides to rest at the corners formed with the longer sides. Furthermore, because the "roofed" rectangle makes a better fit and affords greater inherent torsional rigidity than a flat rectangle, it gives much greater control of rotation of the immobilised bones with respect to the remainder of the spine.

The "roofed" rectangle if the first implanted device to give the spine effective torsional rigidity, therefore allowing immediate mobilisation following surgery, without the need of any external cast or brace.

The shorter sides generally lie in parallel planes, perpendicular to the plane of the longer sides, and each shorter side has two straight portions at an angle to each other of between 90l ° and 110°, with a small radius curve between them and small radius curves at the corners formed with the longer sides.

In addition to providing "roofed" rectangles of different lengths and/or widths, the shorter sides may have different "roof" angles, to suit different sizes of bones and/or bone combinations.

However, "roofed" rectangles as described above, while proving to be a vast improvement compared with previously known devices, particularly in view of their simplicity and secureness, have one disadvantage in that to accommodate the two shorter sides closely between the spinous processes of respectively pairs of adjacent bones of the spine it is necessary to sever the two ligaments between those respective pairs of spinous processes.

One object of the invention is, therefore, to provide an improved device for spinal fixation which additionally provides fixation of a skull to adjacent bones of the spine to assist in holding up the head.

SUMMARY OF THE INVENTION

According to the present invention, a spinal fixation device consists of rod of biocompatible material formed into a loop having two straight spaced coplanar portions intermediate two bights which extend in planes that are not parallel to each other and are not perpendicular to the plane of the straight intermediate portions.

The bights facilitate slight adjustment of the spacing between the straight intermediate portions by increasing or decreasing the bends of the bights, and/or slight adjustment of the shapes of the bights, and/or slight adjustment of the inclinations of the bights to the plane of the straight intermediate portions by increasing or decreasing the bends between the bights and the respective ends of the straight intermediate portions.

A device in accordance with the invention for fixation of a skull to adjacent bones of the spine has one substantially circular bight in a curved plane starting generally perpendicular to the plane of the straight intermediate portions and curving away therefrom, and the other bight is generally V-shaped with its apex extending towards the substantially circular bight, whereby the apex of that V-shape can be accommodated between the adjacent pair of spinous processes closest to the skull against which the substantially circular bight lies (and to which it is secured by means of wires or other strands around or looped through the substantially circular bight and passing through holes in the skull).

BRIEF DESCRIPTION OF THE DRAWINGS

Two embodiments of the invention will now be described, by way of examples only, with reference to the accompanying drawings, in which:

FIG. 5 is a plan view of a device in accordance with the invention for fixation of a skull to adjacent bones of the spine;

FIG. 6 is a side view of the device of FIG. 5;

FIG. 7 is an end view of the device of FIGS. 5 and 6; and

FIG. 8 is a perspective view showing the device of FIGS. 5 to 7 in position relative to the back of a skull and adjacent bones of the spine.

DETAILED DESCRIPTION OF THE ILLUSTRATED EMBODIMENT

Figure 1:
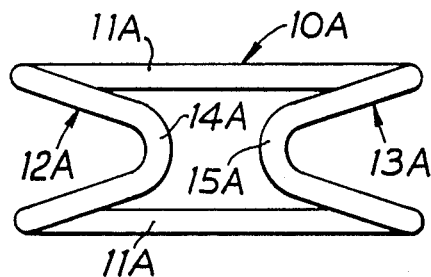
FIG. 1 is a plan view of a spinal fixation device in accordance with the invention.

In the drawings, spinal fixation devices 10A, 10B respectively consist of rods of biocompatible material formed into loops each having two straight spaced coplanar portions 11A, 11B respectively intermediate two bights 12A, 13A and 12B, 13B respectively which extend in planes that are not perpendicular to each other and are not perpendicular to the plane of the respective intermediate portions 11A, 11B.

The bights 12A, 13A or 12B, 13B facilitate slight adjustment of the spacing between the straight intermediate portions 11A or 11B by increasing or decreasing the bends of the bights, and/or slight adjustment of the shapes of the bights, and/or slight adjustment of the inclinations of the bights to the plane of the respective straight intermediate portions by increasing or decreasing the bends between the bights and the respective ends of the respective straight intermediate portions.

Figure 2:
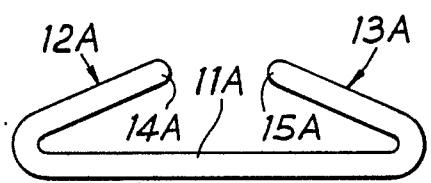
FIG. 2 is a side view of the device of FIG. 1.
Figure 3:
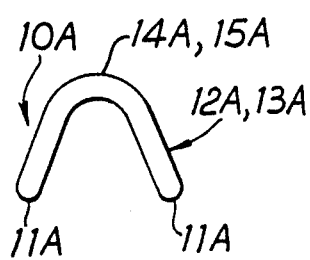
FIG. 3 is an end view of the device of FIGS. 1 and 2.
Figure 4:
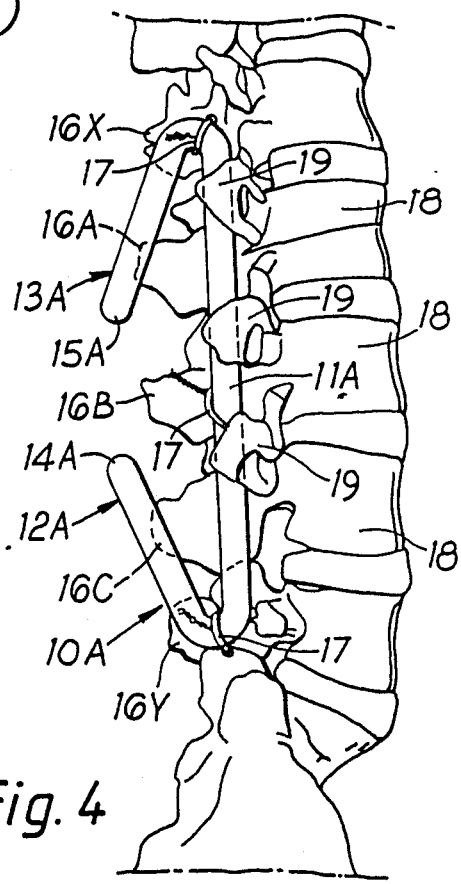
FIG. 4 is a side view showing the device of FIGS. 1 to 3 in position relative to some bones of the spine.

In FIGS. 1 to 3, a spinal fixation device 10A has generally V-shaped bights 12A, 13A with their apices 14a, 15A extending towards each other, whereby those apices can be accommodated between pairs of adjacent spinous processes 16a, 16B and 16B, 16C respectively (see FIG. 4) closer together than would be the case with the shorter sides of the known "roofed" rectangle of the same overall length (i.e., spinous processes 16A, 16X and 16C, 16Y respectively), thus confining the trauma of severed ligaments (not shown) to a lesser length of the spine relative to the overall length of the device 10A.

The device 10A is fixed in place on the spine (see FIG. 4) by means of wires or other strands 17 around or looped through the device and passing through holes in the bones 18 with the straight intermediate portions 11A in firm contact with the transverse processes 19, whereby the bones are immobilised with respect to each other.

In FIGS. 5 to 7, a device 10B for fixation of a skull 20 (FIG. 8) to adjacent bones 21 of the spine has one substantially circular bight 13B in a curved plane starting generally perpendicular to the plane of the straight intermediate portions 11B and curving away therefrom, and the other bight 12B is generally V-shaped with its apex 14B extending towards the substantially circular bight 13B, whereby the apex 14B can be accommodated between the adjacent pair of spinous processes 16D, 16E closest to the skull 20 against which the substantially circular bight 13B lies.

The device 10B is fixed in place by means of wires or other strands 17 around or looped through the device and passing through holes in the skull 20 and the bones 21, whereby the head is held up on the top of the spine.

What I claim is:

1. A spinal fixation device for fixation of a skull to adjacent bones of the spine consisting of a rod of biocompatible material formed into a loop having two straight spaced coplanar portions intermediate two bights which extend in planes that are not parallel to each other and are not perpendicular to the plane of the straight intermediate portions, wherein one of said bights is substantially circular in a curved plane starting generally perpendicular to the plane of the straight intermediate portions and curving away therefrom, and having the other bight generally V-shaped with its apex extending towards the substantially circular bight, whereby the apex of that V-shaped bight can be accommodated between the adjacent pair of spinous processes closest to the skull against which the substantially circular bight lies.

* * * * *